United States Patent [19]

Argoudelis et al.

[11] 3,998,698
[45] Dec. 21, 1976

[54] PROCESS FOR PRODUCING ANTIBIOTIC U-51,640

[75] Inventors: Alexander D. Argoudelis; Fritz Reusser, both of Portage, Mich.

[73] Assignee: The Upjohn Company, Kalamazoo, Mich.

[22] Filed: Apr. 8, 1976

[21] Appl. No.: 674,860

[52] U.S. Cl. .............................................. 195/80 R
[51] Int. Cl.² .......................................... C12D 9/00
[58] Field of Search .................................. 195/80 R

[56] References Cited
OTHER PUBLICATIONS

Journal of Antibiotics, vol. 20, 1967, pp. 66–71.

B542,226, Feb. 1976, Argoudelis et al., 195/80 R.

*Primary Examiner*—A. Louis Monacell
*Assistant Examiner*—Robert J. Warden
*Attorney, Agent, or Firm*—Roman Saliwanchik

[57] ABSTRACT

Antibiotic U-51,640 produced by the controlled fermentation of the microorganism *Streptomyces ficellus* Dietz, sp. n., NRRL 8067. This antibiotic and its acid addition salts are active against Gram-positive and Gram-negative bacteria. Accordingly, they can be used in various environments to eradicate or control such bacteria.

8 Claims, No Drawings

PROCESS FOR PRODUCING ANTIBIOTIC U-51,640

BACKGROUND OF THE INVENTION

The antibiotic of the subject application is produced by the controlled fermentation of the microorganism *Streptomyces ficellus* Dietz, sp. n., NRRL 8067. Previously, as disclosed in application Ser. No. 542,226, filed on Jan. 20, 1975, the subject fermentation was found to produce the new antibiotic U-47,929. Subsequently, the same fermentation was found to produce the new antibiotic U-48,266, and this is disclosed in application Ser. No. 556,573, filed on Mar. 10, 1975. The antibiotic produced by the process of the subject invention, U-51,640, has been found to be identical to nojirimycin (J. Antibiotics 20:66-71, 1967) the structure of which is presented by I

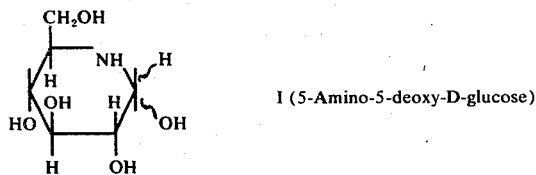

I (5-Amino-5-deoxy-D-glucose)

BRIEF SUMMARY OF THE INVENTION

The antibiotic of the invention, U-51,640 is obtained by culturing *Streptomyces ficellus* Dietz, sp. n., NRRL 8067, in an aqueous nutrient medium under aerobic conditions. Antibiotic U-51,640 and its acid addition salts have the property of adversely affecting the growth of Gram-positive bacteria, for example, *Staphylococcus aureus*, *Sarcina lutea*, and Gram-negative bacteria, for example, *Escherichia coli* and *Proteus vulgaris*. Accordingly, U-51,640 and its acid addition salts can be used alone or in combination with other antibiotic agents to prevent the growth of or reduce the number of bacteria, as disclosed above, in various environments.

DETAILED DESCRIPTION OF THE INVENTION

The process of the subject invention can be used to produce the known antibiotic nojirimycin, which has been given the designation U-51,640. The antibiotic, which will hereinafter be referred to as U-51,640, has the structural formula:

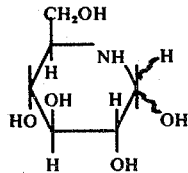

THE MICROORGANISM

The microorganism used for the production of U-51,640 is *Streptomyces ficellus* Dietz, sp. n., NRRL 8067. A subculture of this microorganism can be obtained from the permanent collection of the Northern Regional Research Laboratory, U.S. Department of Agriculture, Peoria, Illinois, U.S.A.

The microorganism of this invention was studied and characterized by Ms. Alma Dietz of the Upjohn Research Laboratories. The taxonomy of *Streptomyces ficellus* Dietz, sp. n., NRRL 8067, is disclosed on pages 7-17 of co-pending U.S. application Ser. No. 542,225, filed on Jan. 20, 1975.

The new compound of the invention is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound of the invention can be effected at any temperature conducive to satisfactory growth of the microorganism, for example, between about 18° and 40° C., and preferably between about 20° and 28° C. Ordinarily, optimum production of the compound is obtained in about 3 to 15 days. The medium normally remains neutral during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating this broth culture with an aliquot from a soil stock, an agar plug stored above liquid $N_2$, or a slant culture. When a young, active vegetative inoculum has thus been secured, it is transferred aseptically to large vessels or tanks. The medium in which the vegetative inoculum is produced can be the same as, or different from, that utilized for the production of the new compound, so long as good growth of the microorganism is obtained.

A variety of procedures can be employed in the isolation and purification of the compound of the subject invention, for example, solvent extraction, partition chromatography, silica gel chromatography, liquid-liquid distribution in a Craig apparatus, adsorption on resins, and crystallization from solvents.

In a preferred recovery process the compound of the subject invention is recovered from the culture medium by separation of the mycelia and undissolved solids by conventional means, such as by filtration or centrifugation. The antibiotic is recovered from the filtered or centrifuged broth by passing the broth over a chromatography column containing a strong-acid cation-exchange resin. This type of resin is made by the nuclear sulfonation of styrene-divinylbenzene beads. Examples of such resins which are suitable for the subject process are Dowex 50 (preferred), and Dowex 50W. Dowex resins can be obtained from the Dow Chemical Company, Midland, Michigan. The column can be eluted with a weak basic solution, for example, a 0.5N aqueous ammonium hydroxide (preferred); aqueous sodium hydroxide, ammonium chloride, pyridine-acetate mixtures also can be used. Fractions from the column are assayed against test organisms as follows:

1. E. coli — specific for U-51,640
2. P. vulgaris-sensitive — specific for U-51,640
3. S. aureus — for detection of U-47,929 and U-51,640
4. S. lutea-sensitive — specific for U-48,266.

Antibiotic U-51,640 is also active against *S. lutea*-sensitive. The zones given by U-51,640 are different than those given by U-48,266. These assays are described infra.

Fractions from the chromatography column, described above, having activity against *E. coli* and *P. vulgaris* can be purified by subjecting them to chromatography using a strong-base anion exchange resin. Suitable resins of this type incorporate a quaternary ammonium functionality. Examples of such resins which can be used in the process of the subject invention are Dowex 1 (preferred), Dowex 11, and Dowex 21K, all available from the Dow Chemical Company, Midland, Michigan. The crosslinkage of the resin can vary from 2 to 8 percent. The column can be eluted with water. Fractions containing only *E. coli* and *P. vulgaris*-sensitive activities contain only antibiotic U-51,640. These fractions can be converted to a bisulfite adduct by passing sulfur dioxide through an aqueous solution of the fractions kept at 0–5° C. After allowing the mixture to stand at room temperature for about two to three hours, a crystalline material is isolated by filtration and identified as antibiotic U-51,640-bisulfite adduct. Antibiotic U-51,640 can be regenerated from this product by dissolving the product in water, adding a strong-base anion-exchange resin, as disclosed above, stirring the mixture for approximately 2–5 hours, and then adding it to a column prepared from the same strong-base anion-exchange resin. The column can be eluted with water and fractions showing activity against *E. coli* and *S. aureus* are combined and freeze-dried to give a relatively pure preparation of antibiotic U-51,640.

Antibiotic U-51,640 is active against *S. aureus* and can be used to disinfect washed and stacked food utensils contaminated with this bacteria; it can also be used as a disinfectant on various dental and medical equipment contaminated with *S. aureus*. Further, antibiotic U-51,640 and its salts can be used to treat laboratory mice infected with *S. aureus*. Still further, antibiotic U-51,640 and its salts can be used as a bacteriostatic rinse for laundered clothes, and for impregnating papers and fabrics; and, they are also useful for suppressing the growth on sensitive organisms in plate assays and other microbiological media.

It is to be understood that the microbiological process disclosed herein, though described in detail with reference to *Streptomyces ficellus* Dietz, sp. n., NRRL 8067, is not limited to this particular microorganism deposit. It is intended that any microorganism meeting the cultural characteristics disclosed herein, or substantial equivalents thereof, wherever deposited in the world, is a part of the subject microbiological process. The following examples are illustrative of the process and products of the subject invention but are not construed as limiting. All percentages are by weight and all solvent mixture proportions are by volume unless otherwise noted.

EXAMPLE 1

Part A. Fermentation

A soil stock of *Streptomyces ficellus* Dietz, sp. n., NRRL 8067, is used to inoculate a series of 500-ml Erlenmeyer flasks, each containing 100 ml of sterile pressed medium consisting of the following ingredients:
Glucose monohydrate: 25 g/litter
Pharmamedia *: 25 g/liter
Tap water q.s.: 1 liter
* Pharmamedia is an industrial grade of cottonseed flour produced by Traders Oil Mill Company, Fort Worth, Texas.

The preseed medium presterilization pH is 7.2. The preseed inoculum is grown for three days at 28° C. on a Gump rotary shaker operating at 250 r.p.m. and having a 2½ inch stroke.

Preseed inoculum (300 ml), prepared as described above, is used to inoculate a seed tank containing 20 liters of sterile seed medium consisting of the following ingredients:
Glucose monohydrate: 10 g/liter
Corn steep liquor: 10 g/liter
Pharmamedia: 2 g/liter
Wilson's Peptone Liquor No. 159 *: 10 g/liter
Tap water: Balance
* Wilson's Peptone Liquor No. 159 is a preparation of hydrolyzed proteins of animal origin.

The inoculated seed medium is incubated at a temperature of 28° C. for 2 days while being agitated at a rate of 400 r.p.m. and aerated at a rate of 10 standard liters per minute with a back pressure of 10 psig.

After 2 days incubation, the seed medium is used to inoculate (the inoculation rate is 5 liters of seed inoculum per 100 liters of fermentation medium) a 250 liter tank fermentation containing sterile fermentation medium consisting of the following ingredients:
Glucose monohydrate: 15 g/liter
Black strap Molasses: 20 g/liter
Starch: 40 g/liter
Pharmamedia: 25 g/liter
$CaCO_3$: 8 g/liter
Tap water q.s.: Balance
ph — 7.2 (presterilization):

The fermentation tank is incubated at a temperature of 28° C., with agitation of 240 r.p.m. and aeration at 80 standard liters per minute with back pressure at 10 psig. Ucon antifoam agent (a synthetic defoamer supplied by Union Carbide, N.Y., N.Y.) is used if needed. Harvest is usually after 3 to 12 days of fermentation.

The fermentation can be monitored by a disc-plate assay using *E. coli* as the test organism. It is conducted with complex nutrient agar (Difco, Bacto-Nutrient Agar)*. Poststerilization pH, ca. 6.8. A unit volume (0.08 ml) of solution containing the substance to be assayed is placed on a 12.7 mm paper disc which is then placed on an agar plate seeded with the assay organism. The agar plate is then incubated for 16 to 18 hours at 32° to 37° C. A biounit (BU) is defined as the concentration of the antibiotic which gives a 20 mm zone of inhibition under the standard assay conditions. Thus, if for example a fermentation beer has to be diluted 1/100 to give a 20 mm zone of inhibition, the potency of such beer is 100 BU/ml.
* (Difco, Bacto-Nutrient Agar)
  Bacto-beef extract: 3 g/liter
  Bacto-peptone: 5 g/liter
  Bacto-agar: 15 g/liter

Part B. Recovery

Antibiotic U-51,640 in recovery beers is detected and assayed by the use of tlc and antibacterial assays. Thin layer chromatograms are run on silica gel plates using 95% aqueous ethanol-water (75:25 v/v) as the solvent system. Bioactivity is detected by bioautography using *E. coli*-seeded agar trays.

The assay using *P. vulgaris*-sensitive has the same medium as used for the *E. coli* assay with the addition of 10 ml of BME vitamin mixture, 100x, per liter. BME vitamin mixture, 100x is supplied by Microbiological Associates, Inc., Bethesda, Maryland.

Whole fermentation beer, obtained as described above, is filtered with the aid of diatomaceous earth as a filter aid. The filter cake is washed with water and the cake is then discarded. Clear beer (30 liters) is adjusted to pH 3.5 with 2N HCl. This material is allowed to stand at room temperature for ca. 2 hours. The acidic clear beer is filtered over diatomaceous earth. The clear solution is adjusted to ca. pH 7.0 with aqueous sodium hydroxide. This solution is also filtered over diatomaceous earth. The filtrate is used for the Dowex 50 chromatography column described below.

Dowex 50 Chromatography

The column is prepared from 2.5 liters of Dowex 50 (x-8) in the hydrogen cycle. The filtrate, prepared as described above, (25 liters) is passed through the column at a rate of 75-80 ml/min. The spent is collected in two fractions (Spent-1; Spent-2). The two spent-fractions are adjusted to pH 7.0 with aqueous sodium hydroxide before spotting.

The column is washed with 10 liters of water at a rate of 75 ml/min. The wash is collected as one fraction.

The column is eluted with 0.5N aqueous ammonium hydroxide. Flow rate is 20 ml/min. Fractions of 20 ml are collected. All antibacterial zones of inhibition, hereinafter shown, are in millimeters (mm).

Testing results follow:

|  | pH | E. coli | S. lutea | S. aureus | P. vulgaris-sensitive |
|---|---|---|---|---|---|
| Start Mat | 7.0 | 21.5 | 26 | 26 | 17 |
| Spent-1 | 7.0 | 0 | 0 | 0 | 0 |
| Spent-2 | 7.0 | 0 | tr | 0 | 0 |
| Aq. Wash | — | 0 | 0 | 0 | 0 |
| 0.5N . NH₄OH |  |  |  |  |  |
| Fraction No. |  |  |  |  |  |
| 10 | 3.95 | 0 | 0 | 0 | 0 |
| 20 | 3.95 | 0 | 0 | 0 | 0 |
| 30 | 3.90 | 0 | 0 | 0 | 0 |
| 40 | 3.95 | 0 | 0 | 0 | 0 |
| 50 | 3.95 | 0 | 0 | 0 | 0 |
| 60 | 4.50 | 0 | 0 | 0 | 0 |
| 70 | 4.38 | 0 | 0 | 0 | 0 |
| 80 | 4.25 | 0 | 0 | 0 | 0 |
| 90 | 4.00 | 0 | 0 | 0 | 0 |
| 100 | 3.96 | 0 | 0 | 0 | 0 |
| 120 | 3.97 | 0 | 0 | 0 | 0 |
| 140 | 3.90 | 0 | 0 | 0 | 0 |
| 160 | 3.95 | 0 | 0 | 0 | 0 |
| 180 | 3.96 | 0 | 0 | 0 | 0 |
| 200 | 4.05 | 0 | 0 | 0 | 0 |
| 220 | 4.20 | 0 | 0 | 0 | 0 |
| 240 | 4.40 | 0 | 0 | 0 | 0 |
| 250 | — | 0 | 24 light | 0 | 0 |
| 260 | 4.91 | 19 | 25 l | 0 | 0 |
| 270 | — | 22.5 | 23 l | 15.5 | 0 |
| 280 | 5.70 | 26 | 27 l | 20 | 0 |
| 290 | — | 28 | 25 | 30 | 16.5 |
| 300 | 7.05 | 33 | 30 | 32.5 | 20 |
| 310 | — | 30 | 29 | 34 | 17 |
| 320 | 6.75 | 32.5 | 28 | 34.5 | 18.5 |
| 330 | — | 33 | 27 | 35 | 19 |
| 340 | 7.0 | 33.5 | 28 | 35 | 19 |
| 350 | — | 33.5 | 27 | 34.5 | 20 |
| 360 | 8.6 | 32.5 | 28 | 34 | 20 |
| 370 | — | 33 | 28 | 33 | 20 |
| 380 | 9.5 | 33 | 26 | 32.5 | 19.5 |
| 390 | — | 33 | 26 | 30 | 18.5 |
| 400 | 10.5 | 30.5 | 25.5 | 29 | 17 |
| *New trays* |  |  |  |  |  |
| 400 | 10.3 | 30 | 33 | 31 | 19 |
| 410 | — | 25 | 31 | 27 | 17 |
| 420 | 10.5 | 16.5 | 31 | 26 | 0 |
| 430 | — | 0 | 29 | 24 | 0 |
| 440 | 10.6 | 0 | 29 | 24 | 0 |
| 450 | — | 0 | 29 | 23.5 | 0 |
| 460 | 10.6 | 0 | 31 | 23 | 0 |
| 470 | — | 0 | 31 | 23.5 | 0 |
| 480 | 10.7 | 0 | 31 | 23.5 | 0 |
| 490 | — | 0 | 31 | 22.5 | 0 |
| 500 | 10.7 | 0 | 31 | 22.5 | 0 |
| 510 | — | 0 | 30 | 21 | 0 |
| 520 | 10.75 | 0 | 29 | 21.5 | 0 |

-continued

| | | | | | |
|---|---|---|---|---|---|
| 530 | — | 0 | 29 | 21.4 | 0 |
| 540 | 10.75 | 0 | 29 | 21 | 0 |
| 550 | — | 0 | 29 | 22 | 0 |
| 560 | 10.80 | 0 | 28 | 21.5 | 0 |
| 570 | — | 0 | 28 | 22.5 | 0 |
| 580 | 10.85 | 0 | 28 | 22.5 | 0 |
| 590 | — | 0 | 27.5 | 23 | 0 |
| 600 | 10.90 | 0 | 28 | 23.5 | 0 |

New trays

| | | | | | |
|---|---|---|---|---|---|
| 610 | — | 0 | 27 | 23 | 0 |
| 620 | 10.75 | 0 | 26 | 22 | 0 |
| 630 | 10.75 | 0 | 26 | 22.5 | 0 |
| 640 | 10.80 | 0 | 25 | 22.5 | 0 |
| 650 | — | 0 | 25 | 22.5 | 0 |
| 660 | 10.80 | 0 | 25 | 23 | 0 |
| 670 | — | 0 | 25 | 22.5 | 0 |
| 680 | 10.90 | 0 | 25 | 22.5 | 0 |
| 690 | — | 0 | 25 | 21.5 | 0 |
| 700 | 10.9 | 0 | 25 | 22.5 | 0 |
| 710 | — | 0 | 25 | 22 | 0 |
| 720 | 10.9 | 0 | 25 | 21.5 | 0 |
| 730 | — | 0 | 25 | 22.5 | 0 |
| 740 | 10.9 | 0 | 24 | 22.5 | 0 |
| 750 | 10.9 | 0 | 24 | 22.5 | 0 |
| 760 | 10.8 | 0 | 23 | 22.5 | 0 |
| 770 | — | 0 | 22 | 22 | 0 |
| 780 | 10.95 | 0 | 22 | 22 | 0 |
| 790 | — | 0 | 21 | 22 | 0 |
| 800 | 10.95 | 0 | 22 | 22 | 0 |
| 810 | — | 0 | 21 | 22 | 0 |
| 820 | 10.95 | 0 | 20 | 21.5 | 0 |
| 830 | — | 0 | 22 | 22 | 0 |
| 840 | 11.0 | 0 | 20.1 | 22 | 0 |
| 850 | — | 0 | 21.5 | 21.5 | 0 |
| 860 | 11.1 | 0 | 20 | 21.5 | 0 |
| 870 | — | 0 | 19.5 | 21 | 0 |
| 880 | 11.1 | 0 | 19 | 20 | 0 |

Fractions 270-400 are combined and freeze-dried to give Preparation ADA-105.1, 60.49 g.

Fractions 401-600 are treated as described above to give Preparation ADA-106.1, 11.58 g.

Fractions 601-800, similarly, give Preparation ADA-108.1, 4.30 g.

Spotting shows the following:

| | | Zones (mm) | | |
|---|---|---|---|---|
| Prep. No. | E. coli | S. lutea | S. aureus | P. vulgaris-sensitive |
| ADA-105.1 | 22 | 24 (light) | 25 | 19 |
| ADA-106.1 | 22(very light) | 33.5 | 27.5 | 15.5 |
| ADA-108.1 | 18(very light) | 34.5 | 33 | — |

Preparation ADA-105.1 is purified further by Dowex-1 chromatography described below.

Dowex-1 Chromatography

The column is prepared from 2.5 liter Dowex-1 (x-4) in the hydroxide form.

The starting material Preparation ADA-105.1, 60 g is dissolved in 1 liter of water (pH found, 7.3). This solution is passed through the column at a rate of 20 ml/min. The spent is collected in 20 ml-fractions (Fr. No. 1-48).

The column is eluted with water at a rate of 15 ml/min. (Fr. No. 49-620). Spotting shows the following:

| | Zones (mm) | | | |
|---|---|---|---|---|
| | S. aureus | E. coli | S. lutea | P. vulgaris-sensitive |
| Start. Mat. (10 mg/ml) | 26 | 25 | 29 | 0 |

-continued

| Fraction No. | | | | |
|---|---|---|---|---|
| 10 | 0 | 0 | 0 | 0 |
| 20 | 0 | 0 | 0 | 0 |
| ↓ | ↓ | ↓ | ↓ | ↓ |
| 220 | 0 | 0 | 0 | 0 |
| 230 | 0 | 0 | 0 | 0 |
| 240 | 19 light | 17 l | 0 | 0 |
| 250 | 21 l | 20 l | tr | 0 |
| 260 | 25 | 24 | 15 | 0 |
| 270 | 30 | 26 | 18 | 0 |

New trays

| | | | | |
|---|---|---|---|---|
| 280 | 31 | 31 | 20.5 | 18 |
| 290 | 32.5 | 32 | 22 | 18 |
| 300 | 32 | 31.5 | 22 | 19 |
| 310 | 32.5 | 31 | 21 | 18 |
| 320 | 31.5 | 21 | 21 | 18 |
| 330 | 31 | 30 | 19 | 18 |
| 340 | 30.5 | 28.5 | 17 | 17 |
| 350 | 29.5 | 28.5 | 17 | 17 |
| 360 | 26.5 | 27 | 16 | tr |
| 370 | 26.5 | 25 | 15 | 0 |
| 380 | 25.5 | 23 | tr | 0 |
| 390 | 24 | 21 | tr | 0 |
| 400 | 18 | 18.5 | tr | 0 |
| 410 | 19.5 | 15 | 0 | 0 |
| 420 | 20.5 | tr | 0 | 0 |
| 430 | 21 | tr | 0 | 0 |
| 440 | 22 | tr | 0 | 0 |

-continued

| | | | | |
|---|---|---|---|---|
| 450 | 21 | tr | 0 | 0 |
| 460 | 21 | tr | 0 | 0 |
| 470 | 19 | tr | 0 | 0 |
| 480 | 20 | tr | 0 | 0 |
| 490 | 18 | tr | 0 | 0 |
| 500 | 18 | 0 | 0 | 0 |
| ↓ | | ↓ | ↓ | ↓ |
| 620 | | 0 | 0 | 0 |

Fractions 260-350 are freeze-dried to give Preparation ADA-112-1A.

Fractions 351-450 are freeze-dried to give Preparation ADA-112-1B.

Preparation ADA-112-1A is dissolved in 50 ml of water and 50 ml of methanol. This solution is mixed with 3 l of acetone. The precipitated material is filtered off and dried (ADA-112.2, 4.20 g).

Preparation ADA-112.2 is found to contain mainly U-51,640. Further purification of antibiotic U-51,640 is obtained by formation of a crystalline "U-51,640-bisulfite adduct" and recovery of pure U-51,640 by treatment with Dowex-1 (OH—) as described infra.

Formation of the "antibiotic U-51,640-bisulfite adduct": Antibiotic U-51,640 as described above, 3.5 g, is dissolved in 20 ml of water. The solution is cooled in ice. Sulfur dioxide is passed through the solution for 2 hours. Formation of crystalline "antibiotic U-51,640-bisulfite adduct" starts after five minutes of reaction. The mixture is allowed to stand at room temperature for 2.5 hours. Crystalline material is isolated by filtration and dried (ADA-12.1, 2.2 g). An additional 220 mg of crystals (ADA-12.2) is obtained from the mother liquors.

Regeneration Antibiotic U-51,640 from the "Antibiotic U-51,640-Bisulfite Adduct".

Two g of Preparation ADA-12.1 is dissolved in 200 ml of water. Dowex-1 (x-4, OH—), 120 ml is added to this solution and the mixture is stirred for 5 hours; it is then added on the top of a column prepared from 500 ml of Dowex-1 (x-4, OH—). The column is eluted with water. Fractions of 20 ml are collected with a rate of 4 ml/min. Testing shows the following:

| Fraction No. | Zone (mm) | |
|---|---|---|
| | E. coli | S. aureus |
| 5 | 0 | 0 |
| 10 | 0 | 0 |
| 15 | 0 | 0 |
| — | — | — |
| — | — | — |
| 30 | 0 | 0 |
| 35 | 22.5 | 19 (very light) |
| 40 | 29 | 30 |
| 45 | 30 | 32 |
| 50 | 21 | 34 |
| 55 | 30 | 34 |
| 60 | 29.5 | 30 |
| 65 | 24.5 | 22 |
| 70 | tr | 0 |
| 75 | 0 | 0 |

Fractions 35-70 are combined and the solution is freeze-dried to give ADA-39.1, 1.12 g pure antibiotic U-51,640.

Antibiotic U-51,640, isolated as described above, is identified as being identical to nojirimycin (5-amino-5-deoxy-D-glucose) (I).

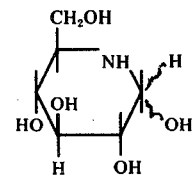

I

The isolation of nojirimycin is described by N. Ishida and K. Kumagai, J. Antibiotics 20: 66–71 (1967).

Identification is obtained by comparing ir, nmr, mass spectral data, and specific rotations of nojirimycin and antibiotic U-51,640.

Both antibiotic U-51,640 and nojirimycin react with acetic anhydride and pyridine to yield II.

$$\text{HO}\diagdown\!\!\!\diagup\!\!\!\diagdown\!\!\!\diagup_{N}\!\!\!\diagdown\text{CH}_2\text{OCOCH}_3$$

II

The structure of II obtained from antibiotic U-51,640 is established by mass, $^{13}$C-nmr and pmr spectra.

Furthermore both antibiotic U-51,640 and nojirimycin react with sulfur dioxide to give the "bisulfite adduct" III.

$$\begin{array}{c}\text{CH}\!\diagup^{\text{OH}}_{\text{SO}_3^-}\\|\\ \text{H}-\text{C}-\text{OH}\\|\\ \text{HO}-\text{C}-\text{H}\\|\\ \text{H}-\text{C}-\text{OH}\\|\\ \text{H}-\text{C}-\text{NH}_3^+\\|\\ \text{CH}_2\text{OH}\end{array}$$

III

III is isolated from nojirimycin by S. Inouye et al. (Tetrahedron 24: 2125–2144, 1968). III, isolated from antibiotic U-51,640 (by reaction with $SO_2$) is found identical to the compound reported by S. Inouye by ir and $^{13}$C-nmr spectroscopy.

We claim:

1. A process for preparing antibiotic U-51,640 which comprises:
  1. cultivating *Streptomyces ficellus* Dietz, sp. n., having the identifying characteristics of NRRL 8067, and mutants thereof, in an aqueous nutrient medium under aerobic conditions until substantial antibiotic activity is imparted to said medium;
  2. filtering a *Streptomyces ficellus* Dietz, sp. n., fermentation beer containing antibiotic U-51,640 to obtain a clear beer;
  3. chromatographing said clear beer on a strong-acid cation-exchange resin and eluting said resin with a weak base solution to obtain fractions active against *E. coli* and *P. vulgaris*-sensitive;
  4. subjecting said fractions active against *E. coli* and *P. vulgaris*-sensitive to chromatography on a strong-base anion-exchange resin and eluting said resin with water to obtain fractions active against *E. coli* and *P. vulgaris*-sensitive;

5. subjecting said fractions active against *E. coli* and *P. vulgaris*-sensitive to a reaction with sulfur dioxide to obtain a crystalline preparation of U-51,640 bisulfite adduct; and, 6. regenerating antibiotic U-51,640 from said bisulfite adduct by passing the same over a strong-base anion-exchange resin and eluting the resin with water to obtain a relatively pure preparation of antibiotic U-51,640.

2. A process, according to claim 1, wherein said strong-acid cation-exchange resin is Dowex-50 (x-8) in the hydrogen cycle which is eluted with 0.5N aqueous ammonium hydroxide.

3. A process, according to claim 1, wherein said strong-acid anion-exchange resin is Dowex-1 (x-4) in the hydroxide form.

4. A process, according to claim 1, for preparing antibiotic U-51,640 which comprises:

1. cultivating *Streptomyces ficellus* Dietz, sp. n., having the identifying characteristics of NRRL 8067, and mutants thereof, in an aqueous nutrient medium under aerobic conditions until substantial antibiotic activity is imparted to said medium;

2. filtering a *Streptomyces ficellus* Dietz, sp. n., fermentation beer containing antibiotic U-51,640 to obtain a clear beer;

3. chromatographing said clear beer on a Dowex-50(x-8) in the hyrdogen cycle and eluting said resin with 0.5N aqueous ammonium hydroxide to obtain fractions active against *E. coli* and *P. vulgaris*-sensitive;

4. subjecting said fractions active against *E. coli* and *P. vulgaris*-sensitive to chromatography on Dowex-1 (x-4) in the hydrogen form and eluting said resin with water to obtain fractions active against *E. coli* and *P. vulgaris*-sensitive;

5. subjecting said fractions active against *E. coli* and *P. vulgaris*-sensitive to a reaction with sulfur dioxide to obtain a crystalline preparation of U-51,640 bisulfite adduct; and 6. regenerating antibiotic U-51,640 from said bisulfite adduct by passing the same over Dowex-1 (x-4) in the hydrogen form and eluting the resin with water to obtain a relatively pure preparation of antibiotic U-51,640.

5. A process for recovering antibiotic U-51,640 from a fermentation beer containing a mixture of antibiotics U-47,929, U-48,266 and U-51,640, which comprises:

1. filtering a *Streptomyces ficellus* Dietz, sp. n., fermentation beer containing antibiotics U-47,929, U-48,266, and U-51,640 to obtain a clear beer;

2. chromatographing said clear beer on a strong-acid cation-exchange resin and eluting said resin with a weak base solution to obtain fractions active against *E. coli* and *P. vulgaris*-sensitive;

3. subjecting said fractions active against *E. coli* and *P. vulgaris*-sensitive to chromatography on a strong-base anion-exchange resin and eluting said resin with water to obtain fractions active against *E. coli* and *P. vulgaris*-sensitive;

4. subjecting said fractions active against *E. coli* and *P. vulgaris*-sensitive to a reaction with sulfur dioxide to obtain a crystalline preparation of U-51,640 bisulfite adduct; and 5. regenerating antibiotic U-51,640 from said bisulfite adduct by passing the same over a strong-base anion-exchange resin and eluting the resin with water to obtain a relatively pure preparation of antibiotic U-51,640.

6. A process, according to claim 5, wherein said strong-acid cation-exchange resin is Dowex-50 (x-8) in the hydrogen cycle which is eluted with 0.5N aqueous ammonium hydroxide.

7. A process, according to claim 5, wherein said strong-base anion-exchange resin is Dowex-1 (x-4) in the hydroxide form.

8. A process, according to claim 5, for recovering antibiotic U-51,640 from a fermentation beer containing a mixture of antibiotics U-47,929, U-48,266 and U-51,640, which comprises:

1. filtering a *Streptomyces ficellus* Dietz, sp. n., fermentation beer containing antibiotics U-47,929, U-48,266 and U-51,640 to obtain a clear beer;

2. chromatographing said clear beer on a Dowex-50 (x-8) in the hydrogen cycle and eluting said resin with 0.5N aqueous ammonium hydroxide to obtain fractions active against *E. coli* and *P. vulgaris*-sensitive;

3. subjecting said fractions active against *E. coli* and *P. vulgaris*-sensitive to chromatography on Dowex-1 (x-4) in the hydrogen form and eluting said resin with water to obtain fractions active against *E. coli* and *P. vulgaris*-sensitive;

4. subjecting said fractions active against *E. coli* and *P. vulgaris*-sensitive to a reaction with sulfur dioxide to obtain a crystalline preparation of U-51,640 bisulfite adduct; and 5. regenerating antibiotic U-51,640 from said bisulfite adduct by passing the same over Dowex-1 (x-4) in the hydrogen form and eluting the resin with water to obtain a relatively pure preparation of antibiotic U-51,640.

* * * * *

UNITED STATES PATENT OFFICE
CERTIFICATE OF CORRECTION

Patent No. 3,998,698           Dated December 21, 1976

Inventor(s) Alexander D. Argoudelis and Fritz Reusser

It is certified that error appears in the above-identified patent and that said Letters Patent are hereby corrected as shown below:

Column 2, line 3, for "542,225" read -- 542,226 --. Column 4, line 15, for "pressed" read -- preseed --. Column 11, line 19, claim 3, for "strong-acid" read -- strong-base --.

Signed and Sealed this

First Day of March 1977

[SEAL]

Attest:

RUTH C. MASON
*Attesting Officer*

C. MARSHALL DANN
*Commissioner of Patents and Trademarks*